(12) United States Patent
Sato et al.

(10) Patent No.: US 9,485,987 B2
(45) Date of Patent: Nov. 8, 2016

(54) AQUEOUS SUSPENDED AGRICULTURAL CHEMICAL COMPOSITION

(71) Applicants: MEIJI SEIKA PHARMA CO., LTD., Tokyo (JP); Nippon Kayaku Co., Ltd., Tokyo (JP)

(72) Inventors: Atsushi Sato, Kanagawa (JP);
Mitsuyuki Yabuzaki, Kanagawa (JP);
Shigeru Ueno, Kanagawa (JP);
Yoshinori Muramatsu, Ibaraki (JP);
Kazuteru Ogawa, Ibaraki (JP);
Hidetoshi Shirakura, Ibaraki (JP)

(73) Assignees: MEIJI SEIKA PHARMA CO., LTD., Tokyo (JP); NIPPON KAYAKU CO., LTD., Tokyo (JP)

( * ) Notice: Subject to any disclaimer, the term of this patent is extended or adjusted under 35 U.S.C. 154(b) by 0 days.

(21) Appl. No.: 14/762,533

(22) PCT Filed: Jan. 29, 2014

(86) PCT No.: PCT/JP2014/051986
§ 371 (c)(1),
(2) Date: Jul. 22, 2015

(87) PCT Pub. No.: WO2014/119620
PCT Pub. Date: Aug. 7, 2014

(65) Prior Publication Data
US 2015/0351384 A1   Dec. 10, 2015

(30) Foreign Application Priority Data

Jan. 30, 2013 (JP) ................................. 2013-015951

(51) Int. Cl.
| | | |
|---|---|---|
| A01N 43/42 | (2006.01) | |
| A01N 25/04 | (2006.01) | |
| A01N 25/30 | (2006.01) | |
| A01N 47/06 | (2006.01) | |

(52) U.S. Cl.
CPC ............... *A01N 25/04* (2013.01); *A01N 25/30* (2013.01); *A01N 47/06* (2013.01)

(58) Field of Classification Search
CPC ....... A01N 25/04; A01N 25/30; A01N 47/06
USPC ......................................................... 514/312
See application file for complete search history.

(56) References Cited

U.S. PATENT DOCUMENTS

| | | | |
|---|---|---|---|
| 6,664,213 B1 | 12/2003 | Furusawa et al. | |
| 7,880,006 B2 * | 2/2011 | Yamamoto | A01N 43/42 546/159 |
| 8,648,195 B2 | 2/2014 | Tanigakiuchi et al. | |
| 2002/0040044 A1 | 4/2002 | Schlatter | |
| 2007/0203181 A1 | 8/2007 | Yamamoto et al. | |

FOREIGN PATENT DOCUMENTS

| | | |
|---|---|---|
| CN | 1368847 A | 9/2002 |
| CN | 1745635 * | 3/2006 |
| CN | 1993328 A | 7/2007 |
| CN | 101108327 A | 1/2008 |
| JP | 9-175904 | 7/1997 |
| JP | 9-208404 | 8/1997 |
| JP | 2002-532395 | 10/2002 |
| JP | 2010-163401 | 7/2010 |
| JP | 2011-16741 | 1/2011 |
| JP | 2011-79741 | 4/2011 |
| JP | 2012-240931 | 12/2012 |
| WO | 00/35284 | 6/2000 |
| WO | 2011/105349 | 9/2001 |
| WO | 2006/013896 | 2/2006 |
| WO | 2012/157205 | 11/2012 |

OTHER PUBLICATIONS

International Preliminary Report on Patentability issued Aug. 13, 2015 in corresponding International Application No. PCT/JP2014/051986.
Taiwan Office Action issued Feb. 10, 2015 in corresponding Taiwan Application No. 103103554 with English translation.
International Search Report mailed Mar. 11, 2014 in corresponding International Application No. PCT/JP2014/051986.
Extended European Search Report issued Jun. 21, 2016 in corresponding European Application No. 14745494.6.
Database WPI, Week 201279, Thomson Scientific, London, GB; AN 2012-Q15811, XP002757932, Nov. 22, 2012.

* cited by examiner

*Primary Examiner* — T. Victor Oh
(74) *Attorney, Agent, or Firm* — Wenderoth, Lind & Ponack, L.L.P.

(57) ABSTRACT

The present invention provides an aqueous suspended agricultural chemical composition comprising an agricultural chemical active ingredient, an alkyl naphthalene sulfonate formalin condensate and one or two or more compounds selected from the group consisting of an alkyl sulfate, a polyoxyalkylene alkyl ether sulfate, an alkyl phosphoric acid and a salt thereof, a polyoxyalkylene alkyl ether phosphoric acid and a salt thereof, and a polyoxyalkylene alkyl ether acetic acid and a salt thereof. The aqueous suspended agricultural chemical composition suppresses the crystal growth of the agricultural chemical active ingredient, and has an excellent effect on pest control and an excellent storage stability.

2 Claims, No Drawings

AQUEOUS SUSPENDED AGRICULTURAL CHEMICAL COMPOSITION

CROSS REFERENCE TO RELATED APPLICATION

The present patent application claims priority of Japanese Patent Application No. 15951/2013 filed on Jan. 30, 2013, the entire disclosure of which is incorporated herein by reference.

FIELD OF INVENTION

The present invention relates to an agricultural chemical composition, and in more detail, relates to an aqueous suspended agricultural chemical composition.

BACKGROUND ART

An aqueous suspended agricultural chemical composition is generally referred to as a flowable formulation, which is a formulation formed by suspending an agricultural chemical active ingredient in a liquid. Since the formulation uses the agricultural chemical active ingredient in a pulverized form, it can prevent the agricultural chemical active ingredient from being separated, precipitated, redispersed, or the like by the addition of supplementary agents such as a surfactant and a thickening agent. Micropulverization of the agricultural chemical active ingredient is an important method for improving the dispersion stability thereof in the liquid and enhancing biological effects (effects on pest control).

However, such micropulverization of the agricultural chemical active ingredient causes crystal growth of the ingredient due to Ostwald ripening during storage, namely the particle size of the ingredient tends to be increased, which not only adversely affects the quality of the formulation due to separation, precipitation, and caking and the like, but also decreases the biological effect. Thus, there is a great need to solve such problems from a practical viewpoint.

In order to solve the problems, there have been many approaches in the past to suppress the crystal growth of the agricultural chemical active ingredient and physically stabilize the formulation.

For example, Japanese Patent Application Laid-Open Publication No. 208404/1997 (Patent Document 1) discloses a suspension composition comprising an agricultural chemical active ingredient in combination with ingredients such as a polycyclic aromatic nonionic/anionic surfactant, which is stated to have good storage stability. Also, Japanese Patent Application Laid-Open Publication No. 532395/2002 (Patent Document 2) discloses that a triazole fungicide can be used with a combination of a surfactant such as tristyrylphenol-ethoxylate or a sulfate thereof and a polymer such as a vinylpyrrolidone homopolymer for the purpose of preventing crystal growth. Furthermore, Japanese Patent Application Laid-Open Publication No. 163401/2010 (Patent Document 3) discloses a composition containing crystalline cellulose, urea, a surfactant and the like in order to suppress the particle growth of the agricultural chemical active compound. However, there were some cases where the above-mentioned surfactants were not suitable for practical use because the surfactants may sometime function in an opposite manner and accelerate the crystal growth instead.

Furthermore, Japanese Patent Application Laid-Open Publication No. 175904/1997 (Patent Document 4) discloses coating of an agricultural chemical active ingredient with a resin compound in order to prevent the particle from being grown or becoming coarse during storage. However, there were some cases where it was difficult to maintain the storage stability because the particle size became large due to the coating of the particle.

Furthermore, Japanese Patent Application Laid-Open Publication No. 16741/2011 (Patent Document 5) discloses an aqueous suspended agricultural chemical composition comprising an agricultural chemical active ingredient in combination with a resin, a sulfonate condensate, and a surfactant. However, there were some cases in the past where the particle growth could not be sufficiently suppressed depending on the type of the agricultural chemical contained in the aqueous suspended agricultural chemical composition.

Furthermore, Japanese Patent Application Laid-Open Publication No. 79741/2011 (Patent Document 6) discloses an agricultural chemical composition which exerts the effect of the agricultural chemical active compound by being spread over a whole rice paddy after first by being brought into contact with leaf surfaces of a crop. However, it has been known that, under some particular storage conditions, the particles of the agricultural chemical active ingredient may grow and become coarse particles; and in fact, there were some cases where the nozzle of the spray was clogged by the agricultural chemical active ingredient when spraying, and the composition could not be practically used as a product. In addition, even if the agricultural chemical active ingredient could be sprayed out, its biological effect (effect on pest control) would be significantly decreased because the particles of the agricultural chemical active ingredient have become coarse.

Therefore, it has been desired to provide a formulation in which the particle growth of the agricultural chemical active ingredient is suppressed for a long time under various storage conditions.

PRIOR ART REFERENCES

Patent Documents

[Patent Document 1] Japanese Patent Application Laid-Open Publication No. 208404/1997
[Patent Document 2] Japanese Patent Application Laid-Open Publication No. 532395/2002
[Patent Document 3] Japanese Patent Application Laid-Open Publication No. 163401/2010
[Patent Document 4] Japanese Patent Application Laid-Open Publication No. 175904/1997
[Patent Document 5] Japanese Patent Application Laid-Open Publication No. 16741/2011
[Patent Document 6] Japanese Patent Application Laid-Open Publication No. 79741/2011

SUMMARY OF THE INVENTION

The present inventors have found that the crystal growth of an agricultural chemical active ingredient can be significantly suppressed by adding an alkyl naphthalene sulfonate formalin condensate and a particular ingredient, namely, an alkyl sulfate, a polyoxyalkylene alkyl ether sulfate, an alkyl phosphoric acid and a salt thereof, a polyoxyalkylene alkyl ether phosphoric acid and a salt thereof, and/or a polyoxyalkylene alkyl ether acetic acid and a salt thereof, to an aqueous suspended agricultural chemical composition. The present invention has been made on the basis of this finding.

Therefore, an object of the present invention is to provide an aqueous suspended agricultural chemical composition which suppresses the crystal growth of an agricultural chemical active ingredient having a quinoline backbone, and has an excellent effect on pest control and storage stability.

In detail, the present invention encompasses the following inventions:

(1) An aqueous suspended agricultural chemical composition comprising
a compound represented by the following Formula (I) or an agriculturally and horticulturally acceptable acid addition salt thereof as an active ingredient,
an alkyl naphthalene sulfonate formalin condensate, and
one or two or more compounds selected from the group consisting of an alkyl sulfate, a polyoxyalkylene alkyl ether sulfate, an alkyl phosphoric acid and a salt thereof, a polyoxyalkylene alkyl ether phosphoric acid and a salt thereof, and a polyoxyalkylene alkyl ether acetic acid and a salt thereof:

[Chemical Formula 1]

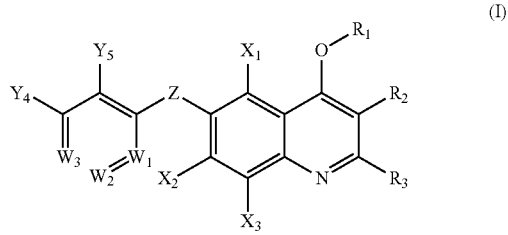

(I)

wherein
$R_1$ is $COR_4'$ or $COOR_5$ (wherein $R_4'$ and $R_5$ are a $C_{1-4}$ alkyl group),
$R_2$ is a $C_{1-4}$ alkyl group,
$R_3$ is a $C_{1-4}$ alkyl group,
$X_1$ and $X_2$ are each independently a hydrogen atom or a $C_{1-4}$ alkyl group optionally substituted with a halogen atom, provided that $X_1$ and $X_2$ are not a hydrogen atom at the same time,
$X_3$ is a hydrogen atom,
$W_1$, $W_2$, and $W_3$ are $C-Y_1$, $C-Y_2$, and $C-Y_3$, respectively,
$Y_1$, $Y_2$, $Y_3$, $Y_4$, and $Y_5$ are each independently a hydrogen atom, a $C_{1-8}$ alkyloxy group, or a halogen atom (wherein the $C_{1-8}$ alkyloxy group is substituted with one or more halogen atoms which may be the same or different, and/or with a $C_{1-4}$ alkyloxy group substituted with one or more halogen atoms which may be the same or different),
provided that at least one of $Y_1$, $Y_2$, $Y_3$, $Y_4$, and $Y_5$ is a $C_{1-8}$ alkyloxy group (wherein the $C_{1-8}$ alkyloxy group is substituted with one or more halogen atoms which may be the same or different, and/or with a $C_{1-4}$ alkyloxy group substituted with one or more halogen atoms which may be the same or different), or
two adjacent groups selected from $Y_1$, $Y_2$, $Y_3$, $Y_4$, and $Y_5$ may be taken together to form $-O-(CH_2)_n-O-$ substituted with one or more halogen atoms (wherein n is 1 or 2), and
Z is an oxygen atom.

(2) The aqueous suspended agricultural chemical composition according to (1), wherein
$R_1$ is $COOR_5$ (wherein $R_5$ is a $C_{1-4}$ alkyl group),
$R_2$ is a $C_{1-4}$ alkyl group,
$R_3$ is a $C_{1-4}$ alkyl group, $X_1$ and $X_2$ are a hydrogen atom or a $C_{1-4}$ alkyl group optionally substituted with a halogen atom, provided that $X_1$ and $X_2$ are not a hydrogen atom at the same time,
$X_3$ is a hydrogen atom,
$W_1$, $W_2$, and $W_3$ are $C-Y_1$, $C-Y_2$, and $C-Y_3$, respectively,
$Y_1$, $Y_2$ and $Y_3$ are each independently a hydrogen atom, a $C_{1-8}$ alkyloxy group, or a halogen atom (wherein the $C_{1-8}$ alkyloxy group is substituted with one or more halogen atoms which may be the same or different),
$Y_4$ and $Y_5$ are each independently a hydrogen atom or a halogen atom, and
Z is an oxygen atom.

(3) The aqueous suspended agricultural chemical composition according to (1), wherein the compound represented by Formula (I) is 2-ethyl-3,7-dimethyl-4-methoxy-carbonyloxy-6-(4-trifluoroparamethoxyphenoxy)quinoline.

(4) The aqueous suspended agricultural chemical composition according to any one of (1) to (3), wherein the polyoxyalkylene alkyl ether sulfate is a polyoxyethylene alkyl ether sulfate.

The aqueous suspended agricultural chemical composition of the present invention can suppress the crystal growth of the agricultural chemical active ingredient contained in the composition, and thus the composition has an excellent effect on pest control and can be stored for a long period with little time-dependent change.

DETAILED DESCRIPTION OF THE INVENTION

The aqueous suspended agricultural chemical composition of the present invention comprises the compound represented by the above Formula (I) or an agriculturally and horticulturally acceptable acid addition salt thereof as an active ingredient (an agricultural chemical active ingredient); and also comprises an alkyl naphthalene sulfonate formalin condensate, and one or two or more compounds selected from the group consisting of an alkyl sulfate, a polyoxyalkylene alkyl ether sulfate, an alkyl phosphoric acid and a salt thereof, a polyoxyalkylene alkyl ether phosphoric acid and a salt thereof, and a polyoxyalkylene alkyl ether acetic acid and a salt thereof. Hereinafter, each of the ingredients contained in the aqueous suspended agricultural chemical composition of the present invention is explained in detail.

A Compound Represented by Formula (I) or an Agriculturally and Horticulturally Acceptable Acid Addition Salt Thereof The compound represented by the above Formula (I) or an agriculturally and horticulturally acceptable acid addition salt thereof contained as an active ingredient (an agricultural chemical active ingredient) in the aqueous suspended agricultural chemical composition of the present invention is not limited in particular, and can be used alone or as a mixture of two or more types thereof. In cases where the compounds are used a mixture, the mixing ratio of them can be selected freely. With respect to the blending ratio of the compound represented by the above Formula (I) or an agriculturally and horticulturally acceptable acid addition salt thereof (an agricultural chemical active ingredient), and other ingredients contained in the aqueous suspended agricultural chemical composition of the present invention, for example, the agricultural chemical active ingredient can be blended in an amount of 0.01 to 60 parts by weight, preferably 0.1 to 50 parts by weight, and more preferably 0.5 to 30 parts by weight per 100 parts by weight of the total weight of the agricultural chemical active ingredient and other ingredients; and the other ingredients can be blended in an amount of 40 to 99.99 parts by weight, preferably 50 to 99.9 parts by weight, and more preferably 70 to 99.5 parts by weight per 100 parts by weight of the total weight of the agricultural chemical active ingredient and other ingredients.

In addition to the compound represented by the above Formula (I) or an agriculturally and horticulturally acceptable acid addition salt thereof, the aqueous suspended agricultural chemical composition of the present invention may further comprise other types of agricultural chemical active ingredients. The other types of agricultural chemical active ingredients which may be contained in the aqueous suspended agricultural chemical composition of the present invention are not limited to a particular ingredient as long as the ingredient is solid at normal temperature and is hardly-soluble or insoluble in water. In cases where the other types of agricultural chemical active ingredients are used in a flowable formulation, it is preferable to use an ingredient which has an aqueous solubility of 100 ppm or less. The other types of agricultural chemical active ingredients which may be used in the aqueous suspended agricultural chemical composition of the present invention include, for example, the ingredients described in "*Agricultural chemical Handbook* 2011" (edited by Japan Plant Protection Association) and "*The Pesticide Manual* 15*th edition*" (published by British Crop Protection Council).

Further, the aqueous suspended agricultural chemical composition of the present invention comprises a compound represented by the following Formula (I) or an agriculturally and horticulturally acceptable acid addition salt thereof as an agricultural chemical active ingredient:

[Chemical Formula 2]

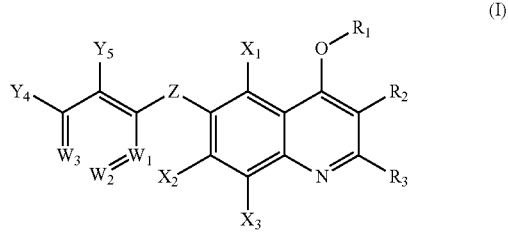

(I)

wherein $R_1$ is $COR_4'$ or $COOR_5$ (wherein $R_4'$ and $R_5$ are a $C_{1-4}$ alkyl group), $R_2$ is a $C_{1-4}$ alkyl group, $R_3$ is a $C_{1-4}$ alkyl group, $X_1$ and $X_2$ are each independently a hydrogen atom or a $C_{1-4}$ alkyl group optionally substituted with a halogen atom, provided that $X_1$ and $X_2$ are not a hydrogen atom at the same time, $X_3$ is a hydrogen atom, $W_1$, $W_2$, and $W_3$ are C—$Y_1$, C—$Y_2$, and C—$Y_3$, respectively, $Y_1$, $Y_2$, $Y_3$, $Y_4$, and $Y_5$ are each independently a hydrogen atom, a $C_{1-8}$ alkyloxy group, or a halogen atom (wherein the $C_{1-8}$ alkyloxy group is substituted with one or more halogen atoms which may be the same or different, and/or with a $C_{1-4}$ alkyloxy group substituted with one or more halogen atoms which may be the same or different), provided that at least one of $Y_1$, $Y_2$, $Y_3$, $Y_4$, and $Y_5$ is a $C_{1-8}$ alkyloxy group (wherein the $C_{1-8}$ alkyloxy group is substituted with one or more halogen atoms which may be the same or different, and/or with a $C_{1-4}$ alkyloxy group substituted with one or more halogen atoms which may be the same or different), or two adjacent groups selected from $Y_1$, $Y_2$, $Y_3$, $Y_4$, and $Y_5$ may be taken together to form —O—$(CH_2)_n$—O— substituted with one or more halogen atoms (wherein n is 1 or 2), and Z is an oxygen atom.

Among the compounds represented by the above Formula (I), a preferable compound has Formula (I) wherein $R_1$ is $COOR_5$ (wherein $R_5$ is a $C_{1-4}$ alkyl group), $R_2$ is a $C_{1-4}$ alkyl group, $R_3$ is a $C_{1-4}$ alkyl group, $X_1$ and $X_2$ are each independently a hydrogen atom or a $C_{1-4}$ alkyl group optionally substituted with a halogen atom, provided that $X_1$ and $X_2$ are not a hydrogen atom at the same time, $X_3$ is a hydrogen atom, $W_1$, $W_2$, and $W_3$ are C—$Y_1$, C—$Y_2$, and C—$Y_3$, respectively, $Y_1$, $Y_2$ and $Y_3$ are each independently a hydrogen atom, a $C_{1-8}$ alkyloxy group, or a halogen atom (wherein the $C_{1-8}$ alkyloxy group is substituted with one or more halogen atoms which may be the same or different), $Y_4$ and $Y_5$ are each independently a hydrogen atom or a halogen atom, and Z is an oxygen atom.

Among the above-mentioned compounds, it is especially preferable that 2-ethyl-3,7-dimethyl-4-methoxycarbonyl-oxy-6-(4-trifluoroparamethoxyphenoxy)quinoline (common name: flometoquin) is contained in the aqueous suspended agricultural chemical composition of the present invention.

The agriculturally and horticulturally acceptable acid addition salt of the compound represented by the above Formula (I) in the aqueous suspended agricultural chemical composition of the present invention includes, for example, a hydrochloride, a nitrate, a sulfate, a phosphate, and an acetate thereof.

The above-mentioned compounds and agriculturally and horticulturally acceptable acid addition salts thereof can be prepared according to the methods disclosed in WO 2006/013896.

The compound represented by the above Formula (I) or an agriculturally and horticulturally acceptable acid addition salt thereof of the present invention shows excellent effects in controlling insect pests and plant fungal pathogens. Thus, the aqueous suspended agricultural chemical composition of the present invention can be used as an insecticide or a fungicide for agriculture and horticulture.

The compound represented by the above Formula (I) or an agriculturally and horticulturally acceptable acid addition salt thereof shows effects in controlling various types of insects.

Such insects are not limited to a particular type, and include preferably lepidopteran insect pests (e.g. Noctuidae such as *Spodoptera litura, Spodoptera exigua, Pseudaletia separata, Mamestra brassicae, Agrotis ipsilon, Trichoplusia* spp., *Heliothis* spp. and *Helicoverpa* spp.; Pyralidae such as *Chilo suppressalis, Cnaphalocrocis medinalis, Ostrinia nubilalis, Hellula undalis, Pediasia teterrellus, Notarcha derogata* and *Plodia interpunctella*; Pieridae such as *Pieris rapae*; Tortricidae such as *Adoxophyes* spp., *Grapholita molesta* and *Cydia pomonella*; Carposinidae such as *Carposina niponensis*; Lyonetiidae such as *Lyonetia* spp.; Lymantriidae such as *Lymantria* spp. and *Euproctis* spp.; Yponomeutidae such as *Plutella xylostella*; Gelechiidae such as *Pectinophora gossypiella*; Arctiidae such as

*Hyphantria cunea*; and Tineidae such as *Tinea translucens* and *Tineola bisselliella*), hemiptera insect pests (e.g. Aphididae such as *Myzus persicae* and *Aphis gossypii*; Delphacidae such as *Laodelphax striatellus, Nilaparvata lugens* and *Sogatella furcifera*; Deltocephalidae such as *Nephotettix cincticeps*; Pentatomidae such as *Trigonotylus caelestialium, Plautia stali* SCOTT, *Nezara viridula* and *Riptortus clavatus*; Aleyrodidae such as *Trialeurodes vaporariorum* and *Bemisia argentifolii*; Coccoidea such as *Pseudococcus comstocki* KUWANA; Tingidae; and Psyllidae), coleopteran insect pests (e.g. Curculionidae such as *Sitophilus zea* ma is, *Lissorhoptrus oryzophilus* and *Callosobruchus chinensis*; Tenebrionidae such as *Tenebrio molitor*; Scarabaeidae such as *Anomala cuprea* and *Anomala rufocuprea*; Chrysomelidae such as *Phyllotreta striolata, Aulacophora femoralis, Leptinotarsa decemlineata, Diabrotica virgifera virgifera* and *Diabrotica undecimpunctata howardi*; *Epilachna* such as *Oulema oryzae, Paederus fuscipes*, Pyraloidea and *Epilachna vigintioctopunctata*; and Cerambycidae), acarian insect pests (e.g. Tetranychidae such as *Tetranychus urticae, Tetranychus kanzawai, Panonychus citri, Panonychus ulmi* and *Oligonychus* spp.; Eriophyidae such as *Aculops lycopersici, Aculops pelekassi* and *Calacarus carinatus; Tarsonemidae* such as *Polyphagotarsonemus latus*; and Acaridae), hymenopteran insect pests (e.g. Tenthredinidae such as *Athalia rosae*), orthopteran insect pests (e.g. Orthoptera), dipteran insect pests (e.g. Muscidae; *Culex; Anopheles*; Chironomidae; Calliphoridae; Sarcophagidae; Fanniidae; Anthomyiidae; Agromyzidae such as *Liriomyza trifolii, Liriomyza sativae* and *Liriomyza bryoniae*; Tephritidae; Phoridae; Drosophilidae; Phlebotominae; Simuliidae; Tabanidae; and Stomoxyinae), thysanoptera insect pests (e.g. *Thrips palmi, Frankliniella occidentalis, Thrips tabaci, Thrips hawaiiensis, Scirtothrips dorsalis, Frankliniella intonsa* and *Ponticulothrips diospyrosi* Haga et Okajima), and phytoparasitic nematodes (e.g. *Meloidogyne; Pratylenchus; Heterodera; Aphelenchoides* such as *Aphelenchoides besseyi*; and *Bursaphelenchus xylophilus* (Steiner & Buhrer) Nickle); and more preferably lepidopteran insect pests, hemipteran insect pests, coleopteran insect pests, acarian insect pests, dipteran insect pests, or thysanoptera insect pests.

The compound represented by the above Formula (I) or an agriculturally and horticulturally acceptable acid addition salt thereof shows effects in controlling various types of plant fungal pathogens. Such plant fungal pathogens are not limited to a particular type, and include typically *Puccinia recondita, Erysiphe graminis, Phytophthora infestans, Pseudoperonospora cubensis, Sphaerotheca fuliginea, Alternaria solani, Botrytis cinerea, Sclerotinia sclerotiorum, Venturia inaequalis, Monilinia fructicola, Colletotrichum gloeosporioides, Cercospora Rhizoctonia solani* and the like; preferably *Sphaerotheca fuliginea, Puccinia recondita, Erysiphe graminis, Alternaria solani, Venturia inaequalis, Monilinia fructicola*, and *Colletotrichum gloeosporioides*; and more preferably *Sphaerotheca fuliginea, Puccinia recondita*, and *Erysiphe graminis*.

The Alkyl Naphthalene Sulfonate Formalin Condensate

The aqueous suspended agricultural chemical composition of the present invention contains an alkyl naphthalene sulfonate formalin condensate. The alkyl naphthalene sulfonate formalin condensate can be used as a dispersant. The alkyl naphthalene sulfonate formalin condensate contained in the aqueous suspended agricultural chemical composition of the present invention is preferably a sodium alkyl naphthalene sulfonate formalin condensate. The number of carbon atoms in the alkyl group of the alkyl naphthalene sulfonate formalin condensate is not limited to a particular number, and it is preferably 1 to 10 and more preferably 1 to 6. Furthermore, the alkyl naphthalene sulfonate formalin condensate contained in the aqueous suspended agricultural chemical composition of the present invention may be an alkyl naphthalene sulfonate formalin polycondensate or sodium methyl naphthalene sulfonate. Furthermore, the alkyl naphthalene sulfonate formalin condensate used herein may be those which are commercially available, for example, Morwet (registered trademark) D-425 Powder, Morwet (registered trademark) D-400 Powder, Morwet (registered trademark) D-809 Powder (all three manufactured by Lion Akzo Co., Ltd.), Politi (registered trademark)N-100K (manufactured by Lion Corporation), Supragil (registered trademark) MNS/90, and Supragil (registered trademark) RM/210-EI (both manufactured by Rhodia Nicca, Ltd.).

The amount of alkyl naphthalene sulfonate formalin condensate contained in the aqueous suspended agricultural chemical composition of the present invention is determined according to the physical properties of the agricultural chemical active ingredient (e.g. water wettability and particle size) and its blending ratio in each type of formulation; and thus it is not limited to a particular amount, and preferably 0.1 to 20 wt % and more preferably 0.5 to 10 wt % based on the total weight of the aqueous suspended agricultural chemical composition.

Other Ingredients

In addition to the above-mentioned agricultural chemical active ingredient and alkyl naphthalene sulfonate formalin condensate, the aqueous suspended agricultural chemical composition of the present invention further comprises one or two or more compounds selected from the group consisting of an alkyl sulfate, a polyoxyalkylene alkyl ether sulfate, an alkyl phosphoric acid and a salt thereof, a polyoxyalkylene alkyl ether phosphoric acid and a salt thereof, and a polyoxyalkylene alkyl ether acetic acid and a salt thereof. The alkyl sulfate, polyoxyalkylene alkyl ether sulfate, alkyl phosphoric acid and a salt thereof, polyoxyalkylene alkyl ether phosphoric acid and a salt thereof, and polyoxyalkylene alkyl ether acetic acid and a salt thereof can be used as a surfactant. In particular, these ingredients can be used as a wetting agent in the aqueous suspended agricultural chemical composition, thereby enhancing water wettability of the aqueous suspended agricultural chemical composition and making it possible to efficiently manufacture the aqueous suspended agricultural chemical composition of the present invention.

According to the present invention, the addition of one or two or more compounds selected from the group consisting of an alkyl sulfate, a polyoxyalkylene alkyl ether sulfate, an alkyl phosphoric acid and a salt thereof, a polyoxyalkylene alkyl ether phosphoric acid and a salt thereof, and a polyoxyalkylene alkyl ether acetic acid and a salt thereof to the above-mentioned agricultural chemical active ingredient and alkyl naphthalene sulfonate formalin condensate makes it possible to provide an aqueous suspended agricultural chemical composition which suppresses the crystal growth of the agricultural chemical active ingredient, and has an excellent effect on pest control and an excellent storage stability.

The polyoxyalkylene used in the aqueous suspended agricultural chemical composition of the present invention is not limited to a particular type as long as the effects of the present invention can be achieved, and it is preferably one compound, or a mixture of two or more selected from the group consisting of a polyoxyethylene and a polyoxypropylene. Furthermore, the salt used herein is not limited to a particular type as long as the effects of the present invention can be achieved; and it is preferably a sodium salt, a potassium salt, a calcium salt, a magnesium salt, an ammonium salt, an ethanolamine salt, a diethanolamine salt, or a triethanolamine salt.

The alkyl sulfate or polyoxyalkylene alkyl ether sulfate can be used as a wetting agent in the aqueous suspended agricultural chemical composition of the present invention.

Further, the alkyl phosphoric acid or polyoxyalkylene alkyl ether phosphoric acid and a salt thereof can be added to the aqueous suspended agricultural chemical composition of the present invention in order to provide an aqueous suspended agricultural chemical composition which suppresses the crystal growth of the agricultural chemical active ingredient, and has an excellent effect on pest control and an excellent storage stability.

Additionally, the polyoxyalkylene alkyl ether acetic acid and a salt thereof can be added to the aqueous suspended agricultural chemical composition of the present invention in order to provide an aqueous suspended agricultural chemical composition which suppresses the crystal growth of the agricultural chemical active ingredient, and has an excellent effect on pest control and an excellent storage stability.

The alkyl sulfate used herein includes, for example, sodium lauryl sulfate, sodium higher alcohol sulfate, and those which are commercially available. The number of carbon atoms in the alkyl group of the alkyl sulfate is not limited to a particular number, and it is preferably 8 to 18. The commercially available products include, for example, EMAL (registered trademark) 10G, EMAL (registered trademark) 10PT, EMAL (registered trademark) 2F-30, EMAL (registered trademark) 2FG, EMAL (registered trademark) 40 Powder (all five manufactured by Kao Corporation), Sorpol (registered trademark) 5029-O (manufactured by TOHO Chemical Industry Co., Ltd.), Newkalgen (registered trademark) LX-C (manufactured by Takemoto Oil & Fat Co., Ltd.), Monogen (registered trademark) Y-100, and Monogen (registered trademark) Y-500T (both manufactured by Dai-ichi Kogyo Seiyaku Co., Ltd.).

The polyoxyalkylene alkyl ether sulfate used herein includes, for example, a sodium polyoxyethylene alkyl ether sulfate, a sodium polyoxyethylene lauryl ether sulfate, an ammonium polyoxyethylene lauryl ether sulfate, an ammonium polyoxyethylene isodecyl ether sulfate, a sodium polyoxyethylene tridecyl ether sulfate, a sodium polyoxyethylene tridecyl ether sulfate, and a triethanolamine polyoxyethylene alkyl ether sulfate. The average number of the added molar units of ethylene oxide in the polyoxyethylene alkyl ether sulfate used herein is, for example, 1 to 30, and preferably 1 to 20. Furthermore, the number of carbon atoms in the alkyl group of the polyoxyalkylene alkyl ether sulfate is not limited to a particular number, and it is preferably 8 to 20 and more preferably 10 to 18. Specifically, it is preferable to use a polyoxyethylene (8) alkyl ether sulfate or a polyoxyethylene (12) alkyl ether sulfate, wherein the number in brackets after the term "polyoxyethylene" represents the average number of the added molar units of ethylene oxide. Specific products of the polyoxyalkylene alkyl ether sulfate include, for example, EMAL (registered trademark) 170J, EMAL (registered trademark) 2703, EMAL (registered trademark) 327, EMAL (registered trademark) D-3-D, EMAL (registered trademark) D-4-D (all five manufactured by Kao Corporation), Sorpol (registered trademark) 5264, Sorpol (registered trademark) 7867, Sorpol (registered trademark) 7868 (all three manufactured by TOHO Chemical Industry Co., Ltd.), Hitenol (registered trademark) LA-10, Hitenol (registered trademark) LA-12, Hitenol (registered trademark) LA-16, Hitenol (registered trademark) PS-06, Hitenol (registered trademark) PS-15, Hitenol (registered trademark) 330T (all six manufactured by Dai-ichi Kogyo Seiyaku Co., Ltd.), Sunnol (registered trademark) LMT-1430, Sunnol (registered trademark) NL-1430, Sunnol (registered trademark) TD-3130 (all three manufactured by Lion Corporation), WITCOLATE (registered trademark) 1050, WITCOLATE (registered trademark) 7093 (both manufactured by Akzo Nobel N.V.), Taipol (registered trademark) NLES-227, Taipol (registered trademark) NLEA-227, Taipol (registered trademark) 22HS, Taipol (registered trademark) DBET-336, Taipol (registered trademark) DBES-327N (all four manufactured by Taiko Oil Chem. Co., Ltd.), Shinorine (registered trademark) SPE-1150, Shinorine (registered trademark) SPE-1250, Shinorine (registered trademark) SPE-1350 (all three manufactured by New Japan Chemical Co., Ltd.), Texapon (registered trademark) N-70, Texapon (registered trademark) N-70 EG, Texapon (registered trademark) ALES 3-70A (all three manufactured by Cognis Corporation), Newkalgen (registered trademark) P-1203S (manufactured by Takemoto Oil & Fat Co., Ltd.), Sandetto (registered trademark) ENR-20, Sandetto (registered trademark) ET, Sandetto (registered trademark) EN, and Sandetto (registered trademark) END (all four manufactured by Sanyo Chemical Industries, Ltd.).

The salt of alkyl phosphoric acid used herein includes, for example, sodium alkyl phosphate, potassium octyl phosphate, potassium lauryl phosphate, potassium stearyl phosphate, and those which are commercially available. Such commercially available products include, for example, Phosphanol (registered trademark) RS-610NA (manufactured by TOHO Chemical Industry Co., Ltd.), GF-185 (manufactured by TOHO Chemical Industry Co., Ltd.), Plysurf (registered trademark) DBS (manufactured by Dai-ichi Kogyo Seiyaku Co., Ltd.), Pionin (registered trademark) A-70, Pionin (registered trademark) A-71-K, and Pionin (registered trademark) A-74 (all three manufactured by Takemoto Oil & Fat Co., Ltd.).

The polyoxyalkylene alkyl ether phosphoric acid used herein includes, for example, a polyoxyethylene alkyl (having 12 to 15 carbon atoms) ether phosphoric acid, a polyoxyethylene tridecyl ether phosphoric acid ester, and a polyoxyethylene lauryl ether phosphoric acid ester. Specific products thereof include, for example, Phosphanol (registered trademark) RS-410, Phosphanol (registered trademark) RS-610, Phosphanol (registered trademark) RS-710 (all three manufactured by TOHO Chemical Industry Co., Ltd.), Plysurf (registered trademark) A212C, and Plysurf (registered trademark) A208B (both manufactured by Dai-ichi Kogyo Seiyaku Co., Ltd.).

The salt of polyoxyethylene alkyl ether phosphoric acid used herein includes, for example, monoethanolamine polyoxyethylene alkyl ether phosphate, potassium polyoxyethylene alkyl ether phosphate, potassium polyoxyethylene alkyl ether phosphate, and those which are commercially available. Such commercially available products include, for example, Plysurf (registered trademark) M208F (manufactured by Dai-ichi Kogyo Seiyaku Co., Ltd.), Electro Stripper (registered trademark) F (manufactured by Kao Corporation), Newkalgen (registered trademark) TG-100, Pionin (registered trademark) A-70-K, Pionin (registered trademark) A-72-DS, Pionin (registered trademark) A-73-DK, and Pionin (registered trademark) A-72-RK (all five manufactured by Takemoto Oil & Fat Co., Ltd.).

The polyoxyalkylene alkyl ether acetic acid used herein includes, for example, polyoxyethylene lauryl ether acetic acid and those which are commercially available. Such commercially available products include, for example, Kaoakypo (registered trademark) RLM-45, Kaoakypo (registered trademark) RLM-100 (both manufactured by Kao Corporation), Beaulight (registered trademark) LCA-H, and Beaulight (registered trademark) LCA-25NH (both manufactured by Sanyo Chemical Industries, Ltd.).

The salt of polyoxyalkylene alkyl ether acetic acid used herein includes, for example, sodium polyoxyethylene lauryl ether acetate and those which are commercially available. Such commercially available products include, for example, Neohitenol (registered trademark) ECL-45 (manufactured by Dai-ichi Kogyo Seiyaku Co., Ltd.), Kaoakypo (registered trademark) RLM-45NV, Kaoakypo (registered trademark) RLM-100NV (both manufactured by Kao Corporation), Beaulight (registered trademark) LCA, Beaulight (registered trademark) LCA-25N, and Beaulight (registered trademark) ECA (all three manufactured by Sanyo Chemical Industries, Ltd.).

The amount of these ingredients contained in the aqueous suspended agricultural chemical composition of the present invention is determined according to the physical properties of the agricultural chemical active ingredient (e.g. water wettability and particle size) and its blending ratio in each type of formulation; and thus it is not limited to a particular amount, and preferably 0.1 to 15 wt % and more preferably 0.5 to 10 wt % based on the total weight of the aqueous suspended agricultural chemical composition.

In cases where these ingredients are used in combination with the sodium alkyl naphthalene sulfonate formalin condensate, one of these ingredients may be used alone or two or more of these ingredients may be used together.

The present invention can exhibit sufficient effects on the suppression of the crystal growth by combining the alkyl naphthalene sulfonate formalin condensate with the above-mentioned ingredients. The effect of suppressing the crystal growth can be further enhanced by combining the alkyl naphthalene sulfonate formalin condensate with especially a polyoxyalkylene alkyl ether sulfate, a polyoxyalkylene alkyl ether phosphoric acid and a salt thereof, a polyoxyalkylene alkyl ether acetic acid and a salt thereof, or an alkyl sulfate. In particular, the alkyl naphthalene sulfonate formalin condensate is combined with preferably a polyoxyalkylene alkyl ether sulfate, and more preferably a polyoxyethylene alkyl ether sulfate.

In addition to the above-mentioned ingredients, the aqueous suspended agricultural chemical composition of the present invention can further comprise a supplementary agent as explained hereinafter, as long as the added amount does not impair the effects of the present invention.

The supplementary agent which can be used in the present invention includes, for example, a surfactant, a thickening agent, an antifoaming agent, an antifreezing agent, and an antifungal agent.

The surfactant which can be used in the aqueous suspended agricultural chemical composition of the present invention includes a nonionic surfactant and an anionic surfactant.

The nonionic surfactant used herein includes, for example, a sorbitan fatty acid ester, a polyoxyalkylene sorbitan fatty acid ester, a sucrose fatty acid ester, a polyoxyalkylene fatty acid ester, a polyoxyalkylene resin acid ester, a polyoxyalkylene castor oil, a polyoxyalkylene hydrogenated castor oil, a polyoxyalkylene alkyl ether, a polyoxyalkylene alkyl phenyl ether, a polyoxyethylene-polyoxypropylene block polymer, a polyoxyethylene polyoxypropylene alkyl ether, a polyoxyalkylene alkyl amine, a polyoxyalkylene fatty acid amide, a polyoxyalkylene styryl phenyl ether, a silicone-based surfactant, and an acetylene glycol-based surfactant.

The anionic surfactant used herein includes, for example, a polyoxyalkylene alkyl phenyl ether sulfate, a polyoxyalkylene styryl phenyl ether sulfate, a polyoxyethylene-polyoxypropylene block polymer sulfate, an alkane sulfonate, an alpha-olefin sulfonate, a dialkyl sulfosuccinate, an alkylbenzene sulfonate, an alkyl diphenyl ether disulfonate, a lignin sulfonate, a polyoxyalkylene alkyl phenyl ether sulfonate, a fatty acid salt, an N-methyl fatty acid sarcosinate, a resinate, a polyoxyalkylene alkyl phenyl ether phosphate, a polyoxyalkylene styryl phenyl ether phosphate, and a polycarboxylate-based surfactant. It should be noted that the polyoxyalkylene is not limited to a particular type as long as the effects of the present invention can be achieved; and it is preferably one compound, or a mixture of two or more compounds selected from the group consisting of a polyoxyethylene and a polyoxypropylene.

The surfactant which can be used in the present invention should not be limited to those shown above, and can be used alone or in combination with two or more.

The thickening agent which can be contained in the aqueous suspended agricultural chemical composition of the present invention includes an organic thickening agent, an inorganic thickening agent, and a mixture thereof.

The organic thickening agent used herein includes, for example, a xanthan gum, a welan gum, a rhamsan gum, a diutan gum, a guar gum, a locust bean gum, a tragacanth gum, pullulan, pectin, arabinogalactan, casein, a tara gum, gum arabic, a tamarind gum, a karaya gum, starch, strach derivatives (e.g. dextrin), sodium alginate, carrageenan, cellulose derivatives (e.g. carboxymethylcellulose, hydroxyethylcellulose, carboxyethylcellulose, methylcellulose, hydroxypropylcellulose, and hydroxyethylcellulose), a polyvinylpyrrolidone, a polyvinyl alcohol, an acrylic-based polymer, and a water-soluble cellulose ether; and preferably a xanthan gum. Commercially available products can also be used as the organic thickening agent. Such commercially available products include, for example, Rhodopol (registered trademark) G, Rhodopol (registered trademark) 23 (both manufactured by Rhodia Nicca, Ltd.), Kelzan (registered trademark), Kelzan (registered trademark) S, and Keizan (registered trademark) ASX (all three manufactured by Sansho Chemical Industries Co., Ltd.).

The inorganic thickening agent used herein includes, for example, smectite-based clay minerals and colloidal silica; and more preferably a purified bentonite. Commercially available products can also be used as the inorganic thickening agent. Such commercially available products include, for example, Kunipia (registered trademark) F (manufactured by Kunimine Industries Co., Ltd.), Wenger (registered trademark), Wenger (registered trademark) FW, and Wenger (registered trademark) HVP (all three manufactured by Hojun Co., Ltd.).

The antifoaming agent which may be contained in the aqueous suspended agricultural chemical composition of the present invention includes, for example, silicone-based agents and acetylene-based agents (e.g. a silicone oil, a silicone emulsion and a polydimethylsiloxane). Commercially available products can also be used as the antifoaming agent. Such commercially available products include, for example, silicone-based agents such as Antifoam (registered trademark) E-20 (manufactured by Kao Corporation), Pronal (registered trademark) EX-300 (manufactured by TOHO Chemical Industry Co., Ltd.), KM-72, KM-73, KM-98 (all three manufactured by Shin-Etsu Chemical Co., Ltd.); and acetylene-based agents such as Surfynol (registered trademark) 104PG-50, Surfynol (registered trademark) 420, and Surfynol (registered trademark) DF37 (all three manufactured by Nissin Chemical Industry Co., Ltd.).

The antifreezing agent which may be contained in the aqueous suspended agricultural chemical composition of the present invention includes, for example, alkylene glycol-based agents (e.g. ethylene glycol and propylene glycol), glycerol, and urea.

The antifungal agent which may be contained in the aqueous suspended agricultural chemical composition of the present invention includes, for example, nitrogen- and sulfur-containing organic compounds (e.g. 1,2-benzisothiazolin-3-one, 2-benzisothiazolin-3-one, 5-chloro-2-methyl-4-isothiazolin-3-one, and 2-methyl-4-isothiazolin-3-one); and ascorbic acid, hexamethylenetetramine, sodium propionate, sorbic acid, sulfurous acid solution, paraformaldehyde, benzoic acid, propyl parahydroxybenzoate, butyl paraoxybenzoate, methyl parahydroxybenzoate, sodium benzoate, ascorbic acid, ascorbic acid palmitate, sodium 1,1'-biphenyl-2-olate, formalin solution, sorbic acid, potassium sorbate, and bromine-containing organic compounds. Commercially available products can also be used as the antifungal agent. Such commercially available products include, for example, Mekkinsu (registered trademark) P (manufactured by Ueno Fine Chemicals Industry, Ltd.), Proxel (registered trademark) GXL (S) (manufactured by Avecia Co., Ltd.), Biokiller (registered trademark) LS (manufactured by KI Chemical Industry Co., Ltd.), and a mixture of a nitrogen- and sulfur-containing organic compound and a bromine-containing organic compound such as Biohope (registered trademark) and Biohope (registered trademark) L (manufactured by KI Chemical Industry Co., Ltd.).

Other than the above-mentioned supplementary agents, if necessary, an antioxidant, an ultraviolet absorber, a colorant, an adjuvant, a co-solvent, a specific gravity adjuster, and the like can be added to the aqueous suspended agricultural chemical composition of the present invention. Furthermore, the supplementary agent which can be used herein includes various types of substances and includes those which are not exemplified herein, as long as the effects of the present invention can be achieved.

The aqueous suspended agricultural chemical composition of the present invention can be prepared by adding water as a solvent to the above-mentioned agricultural chemical active ingredient, alkyl naphthalene sulfonate formalin condensate, and alkyl sulfate or other compounds.

The aqueous suspended agricultural chemical composition of the present invention can be prepared according to a general production method of flowable formulation. In detail, it can be prepared by a method comprising a first step of milling an agricultural chemical active ingredient alone or together with a supplementary agent (e.g. a surfactant), and then a second step of mixing it with the remaining ingredients (e.g. a surfactant, a thickening agent, an antifreezing agent, an antifungal agent, and an antifoaming agent); or a method comprising a step of milling an agricultural chemical active ingredient together with a supplementary agent (e.g. a surfactant, a thickening agent, an antifreezing agent, an antifungal agent, and an antifoaming agent).

According to a preferred embodiment of the production method of the aqueous suspended agricultural chemical composition of the present invention, there is provided a production method of an aqueous suspended agricultural chemical composition comprising a step of adding the alkyl naphthalene sulfonate formalin condensate and the one or two or more compounds selected from the group consisting of an alkyl sulfate, a polyoxyalkylene alkyl ether sulfate, an alkyl phosphoric acid, a polyoxyalkylene alkyl ether phosphoric acid and a salt thereof, and a polyoxyalkylene alkyl ether acetic acid and a salt thereof to the compound represented by the above Formula (I) or an agriculturally and horticulturally acceptable acid addition salt thereof.

The production method of the aqueous suspended agricultural chemical composition of the present invention includes, for example, a method comprising steps of mixing an alkyl sulfate or a polyoxyethylene alkyl ether sulfate and an alkyl naphthalene sulfonate formalin condensate in water, adding an agricultural chemical active ingredient and optionally other supplementary agents thereto, pulverizing the mixture to a desirable particle size in a wet grinding mill using glass beads or the like, adding supplementary agents such as a thickening agent thereto, and then mixing the whole or a method comprising steps of dry milling an agricultural chemical active ingredient with supplementary agents such as a surfactant, adding the mixture to a solution prepared by dissolving an alkyl sulfate or a polyoxyethylene alkyl ether sulfate, an alkyl naphthalene sulfonate formalin condensate, and other supplementary agents in water, pulverizing the mixture to a desired particle size in a wet grinding mill using glass beads or the like, adding supplementary agents such as a thickening agent thereto, and then mixing the whole.

Typically, it is preferable to finely grind the particle size of the agricultural chemical active ingredient to approximately 0.5 to 3 μm. The particle size can be varied depending on the physical properties of the agricultural chemical active ingredient.

The grinding mill which can be used in manufacturing the aqueous suspended agricultural chemical composition of the present invention includes, for example, wet grinding mills such as Batch-type Beads Mill, Dyno Mill, Aquamizer, Attritor, Pearl Mill, Agitator Mill, CoBall Mill, Spike mill, Apex Mill, Sand Grinder Mill, Visco Mill, Glen Mill, Star Mill and SC Mill, and specifically Dyno Mill Multi-Lab (manufactured by Shinmaru Enterprises corporation), Ready Mill BSG-1/16 (manufactured by IMEX Co., Ltd.), and Ultra Apex Mill UAM-05 (manufactured by Kotobuki Industries Co., Ltd.). The beads used herein includes, for example, glass beads, special glass beads (low-alkali or alkali-free), zirconia beads, zircon beads (zirconia-silica-based ceramics), alumina beads, titania beads, SiAlON beads, silicon nitride beads, and Ottawa sands. The particle size of the beads used herein is in the range of preferably 0.01 to 1.5 mm, and more preferably 0.1 to 1.0 mm. It is possible to manufacture a flowable having a small volume median diameter by using beads having a small particle size.

The particle size of the agricultural chemical active ingredient contained in the aqueous suspended agricultural chemical composition of the present invention strongly influences the effect on pest control. Thus, it is important to confirm that the crystal growth of the agricultural chemical active ingredient has not progressed.

The particle size of the agricultural chemical active ingredient can be represented by the volume median diameter. The volume median diameter used herein represents an average particle size based on volume, and is calculated by using a cumulative curve (wherein 100% denotes the total volume of the population) and is defined as the particle size at which the cumulative curve is 50%. The volume median diameter can be measured by laser diffraction particle size analyzers such as SALD-2200 (manufactured by Shimadzu Corporation).

EXAMPLES

Hereinafter, the present invention is explained in detail by showing some working examples, but the scope of the present invention should not be limited thereto. In addition, hereinafter, the number in brackets after the term "polyoxyethylene" represents the average number of the added molar units of ethylene oxide.

Example 1

3.0 wt % polyoxyethylene (8) alkyl ether sulfate (trade name: Sorpol (registered trademark) 7867, source: TOHO Chemical Industry Co., Ltd.), 3.0 wt % Morwet (registered trademark) D-425 Powder (sodium alkyl naphthalene sulfonate formalin condensate, manufactured by Lion Akzo Co., Ltd.), 10.0 wt % propylene glycol (trade name: industrial propylene glycol, source: Adeka Corporation), 0.35 wt % Kunipia (registered trademark) F (purified bentonite, source: Kunimine Industries Co., Ltd.), 0.3 wt % Antifoam (registered trademark) E-20 (silicone-based antifoaming agent, source: Kao Corporation), and 52.4 wt % water were added to a beaker, and the mixture was mixed using a magnetic stirrer. To the mixture was added 10.75 wt % 2-ethyl-3,7-dimethyl-4-methoxy-carbonyloxy-6-(4-trifluoroparamethoxyphenoxy)quinoline (hereinafter, optionally referred to as "flometoquin" (common name)) (purity 95.8%) as an agricultural chemical active ingredient, the resultant mixture was mixed and stirred using a mixer (Tornado PM-201, manufactured by AS ONE Corporation), glass beads having a diameter of 0.5 to 0.7 mm (glass beads BZ-06, manufactured by AS ONE Corporation) were added thereto, and then the mixture was wet milled until the average particle size thereof became approximately 1.2 μm.

To the milled solution were added 0.2 wt % Antifoam (registered trademark) E-20 (silicone-based antifoaming agent, source: Kao Corporation) and 20 wt % aqueous 1% xanthan gum solution prepared in advance (wherein 1 wt % Rhodopol (registered trademark) 23 (xanthan gum, source: Rhodia Nicca, Ltd.) and 1.5 wt % Proxel (registered trademark) GXL (S) (1,2-benzisothiazolin-3-one, source: Avecia Co., Ltd.) were dissolved in 97.5 wt % water), and then the mixture was mixed using a magnetic stirrer to give a flowable formulation containing 10.3 wt % flometoquin.

Example 2

A flowable formulation containing 10.3 wt % flometoquin was prepared by using the same starting materials and procedure in Example 1 except that the polyoxyethylene (8) alkyl ether sulfate used in Example 1 was replaced with polyoxyethylene (12) alkyl ether sulfate (trade name: Sorpol (registered trademark) 7868, source: TOHO Chemical Industry Co., Ltd.).

Example 3

A flowable formulation containing 10.3 wt % flometoquin was prepared by using the same starting materials and procedure in Example 1 except that the polyoxyethylene (8) alkyl ether sulfate used in Example 1 was replaced with polyoxyethylene (16) alkyl ether sulfate (trade name: HITENOL (registered trademark) LA-16, source: DAIICHI KOGYO SEIYAKU Co., Ltd.).

Example 4

A flowable formulation containing 10.3 wt % flometoquin was prepared by using the same starting materials and procedure in Example 1 except that the polyoxyethylene (8) alkyl ether sulfate used in Example 1 was replaced with polyoxyethylene (2) alkyl ether sulfate (trade name: EMAL (registered trademark) 270J, source: Kao Corporation.).

Example 5

A flowable formulation containing 10.3 wt % flometoquin was prepared by using the same starting materials and procedure in Example 1 except that the polyoxyethylene (8) alkyl ether sulfate used in Example 1 was replaced with alkyl sulfate (trade name: EMAL (registered trademark) 10PT, source: Kao Corporation.).

Example 6

A flowable formulation containing 10.3 wt % flometoquin was prepared by using the same starting materials and procedure in Example 1 except that the polyoxyethylene (8) alkyl ether sulfate used in Example 1 was replaced with polyoxyethylene (12) alkyl ether sulfate (trade name: Sorpol (registered trademark) 7868, source: TOHO Chemical Industry Co., Ltd.), the amount of sodium alkyl naphthalene sulfonate formalin condensate (Morwet (registered trademark) D-425 Powder, source: Lion Akzo Co., Ltd.) used in Example 1 was increased from 3 wt % to 5 wt %, and the amount of water was changed to 50.4 wt %.

Example 7

A flowable formulation containing 10.3 wt % flometoquin was prepared by using the same starting materials and procedure in Example 1 except that the polyoxyethylene (8) alkyl ether sulfate used in Example 1 was replaced with polyoxyethylene (4.5) alkyl ether acetate (trade name: NEOHITENOL (registered trademark) ELC-45, source: DAIICHI KOGYO SEIYAKU Co., Ltd.).

Example 8

A flowable formulation containing 10.3 wt % flometoquin was prepared by using the same starting materials and procedure in Example 1 except that the polyoxyethylene (8) alkyl ether sulfate used in Example 1 was replaced with polyoxyethylene (6) alkyl ether phosphate (trade name: PHOSPHANOL (registered trademark) RS-610NA, source: TOHO CHEMICAL INDUSTRY Co., Ltd.).

Example 9

A flowable formulation containing 10.3 wt % flometoquin was prepared by using the same starting materials and procedure in Example 1 except that the polyoxyethylene (8) alkyl ether sulfate used in Example 1 was replaced with alkyl phosphate (trade name: GF-185, source: TOHO CHEMICAL INDUSTRY Co., Ltd.).

Example 10

2.4 wt % polyoxyethylene (12) alkyl ether sulfate (trade name: Sorpol (registered trademark) 7868, source: TOHO Chemical Industry Co., Ltd.), 3.0 wt % Morwet (registered trademark) D-425 Powder (sodium alkyl naphthalene sulfonate formalin condensate, source: Lion Akzo Co., Ltd.), 10 wt % propylene glycol (trade name: industrial propylene glycol, source: Adeka Corporation), 0.35 wt % Kunipia (registered trademark) F (purified bentonite, source: Kunimine Industries Co., Ltd.), 0.3 wt % Antifoam (registered trademark) E-20 (silicone-based antifoaming agent, source: Kao Corporation) and 52.0 wt % water were added to a beaker, and the mixture was mixed using a magnetic stirrer. To the mixture was added 18.75 wt % mixed compound (prepared by mixing 10.75 wt % flometoquin (purity 95.8%) and 1 wt % Sorpol (registered trademark) 5050 (dialkyl sulfosuccinate, source: TOHO Chemical Industry Co., Ltd.) and coarse grinding using a juicer mixer), the mixture was mixed and stirred using a mixer (Tornado PM-201, manufactured by AS ONE Corporation), glass beads having a diameter of 0.5 to 0.7 mm (glass beads BZ-06, manufactured by AS ONE Corporation) were added thereto, and then the resultant mixture was wet milled until the average particle size thereof became approximately 1.2 µm.

To the milled solution were added 0.2 wt % Antifoam (registered trademark) E-20 (silicone-based antifoaming agent, source: Kao Corporation) and 20 wt % aqueous 1% xanthan gum solution prepared in advance (wherein 1 wt % Rhodopol (registered trademark) 23 (xanthan gum, source: Rhodia Nicca, Ltd.) and 1.5 wt % Proxel (registered trademark) GXL (S) (1,2-benzisothiazolin-3-one, source: Avecia Co., Ltd.) were dissolved in 97.5 wt % water), and then the mixture was mixed using a magnetic stirrer to give a flowable formulation containing 10.3 wt % flometoquin.

Example 11

A flowable formulation containing 10.3 wt % flometoquin was prepared by using the same starting materials and procedure in Example 1 except that the amount of the polyoxyethylene (12) alkyl ether sulfate used in Example 2 was decreased from 3M wt % to 2.4 wt %, 1 wt % alkyl sulfate (trade name: EMAL (registered trademark) 10PT, source: Kao Corporation) was newly added to the formulation, and the amount of water was changed to 52.0 wt %.

Example 12

A flowable formulation containing 10.3 wt % flometoquin was prepared by using the same starting materials and procedure in Example 1 except that the polyoxyethylene (8) alkyl ether sulfate used in Example 1 was replaced with polyoxyethylene (12) alkyl ether sulfate (trade name: Sorpol (registered trademark) 7868, source: TOHO Chemical Industry Co., Ltd.), the amount of Morwet (registered trademark) D-425 Powder (sodium alkyl naphthalene sulfonate formalin condensate, source: Lion Akzo Co., Ltd.) used was decreased from 3 wt % to 1.5 wt %, and the amount of water used was changed to 53.9 wt %.

Example 13

A flowable formulation containing 10.3 wt % flometoquin was prepared by using the same starting materials and procedure in Example 1 except that the amount of polyoxyethylene (12) alkyl ether sulfate used in Example 2 was decreased from 3.0 wt % to 1.5 wt % and the amount of water was changed to 53.9 wt %.

Example 14

A flowable formulation containing 10.3 wt % flometoquin was prepared by using the same starting materials and procedure in Example 1 except that the amount of polyoxyethylene (12) alkyl ether sulfate used in Example 2 was increased from 3.0 wt % to 4.0 wt % and the amount of water was changed to 51.4 wt %.

Comparative Example 1

3.0 wt % polyoxyethylene (14) styryl phenyl ether sulfate (trade name: Sorpol (registered trademark) T-15SPG, source: TOHO Chemical Industry Co., Ltd.), 3.0 wt % Morwet D-425 Powder (sodium alkyl naphthalene sulfonate formalin condensate, source: Lion Akzo Co., Ltd.), 10.0 wt % propylene glycol (trade name: industrial propylene glycol, source: Adeka Corporation), 0.35 wt % Kunipia (registered trademark) F (purified bentonite, source: Kunimine Industries Co., Ltd.), 0.3 wt % Antifoam (registered trademark) E-20 (silicone-based antifoaming agent, source: Kao Corporation) and 52.4 wt % water were added to a beaker, and the mixture was mixed using a magnetic stirrer. To the mixture was added 10.75 wt % 2-ethyl-3,7-dimethyl-4-methoxycarbonyloxy-6-(4-trifluoropara-methoxyphenoxy)quinoline (hereinafter, optionally referred to as "flometoquin" (common name)) (purity 95.8%), the resultant mixture was mixed and stirred using a mixer (Tornado PM-201, manufactured by AS ONE Corporation), glass beads having a diameter of 0.5 to 0.7 mm (glass beads BZ-06, manufactured by AS ONE Corporation) were added thereto, and then the mixture was wet milled under monitoring the particle size thereof until the average particle size thereof became approximately 1.2 µm.

To the milled solution were added 0.2 wt % Antifoam (registered trademark) E-20 (silicone-based antifoaming agent, source: Kao Corporation) and 20 wt % aqueous 1% xanthan gum prepared in advance (trade name: Rhodopol (registered trademark) 23, source: Rhodia Nicca, Ltd.) solution, and then the mixture was mixed using a magnetic stirrer to give a flowable formulation containing 10.3 wt % flometoquin.

Comparative Example 2

A flowable formulation containing 10.3 wt % flometoquin was prepared by using the same starting materials and procedure in Comparative Example 1 except that the polyoxyethylene (14) styryl phenyl ether sulfate used in Comparative Example 1 was replaced with polyoxyethylene (14) styryl phenyl ether (trade name: Sorpol (registered trademark) T-15, source: TOHO Chemical Industry Co., Ltd.).

Comparative Example 3

A flowable formulation containing 10.3 wt % flometoquin was prepared by using the same starting materials and procedure in Comparative Example 1 except that the polyoxyethylene (14) styryl phenyl ether sulfate used in Comparative Example 1 was replaced with polyoxyethylene (19) styryl phenyl ether (trade name: Sorpol (registered trademark) T-20, source: TOHO Chemical Industry Co., Ltd.).

Comparative Example 4

A flowable formulation containing 10.3 wt % flometoquin was prepared by using the same starting materials and procedure in Comparative Example 1 except that the polyoxyethylene (14) styryl phenyl ether sulfate used in Comparative Example 1 was replaced with polyoxyethylene (18)

polyoxypropylene (12) alkyl ether (trade name: Pepol (registered trademark) A-0858, source: TOHO Chemical Industry Co., Ltd.).

Comparative Example 5

A flowable formulation containing 10.3 wt % flometoquin was prepared by using the same starting materials and procedure in Comparative Example 1 except that the polyoxyethylene (14) styryl phenyl ether sulfate used in Comparative Example 1 was replaced with polyoxyethylene (26) polyoxypropylene (30) block polymer (trade name: Pepol (registered trademark) B-184, source: TOHO Chemical Industry Co., Ltd.).

Comparative Example 6

A flowable formulation containing 10.3 wt % flometoquin was prepared by using the same starting materials and procedure in Comparative Example 1 except that the polyoxyethylene (14) styryl phenyl ether sulfate used in Comparative Example 1 was replaced with polyoxyethylene (8) alkyl ether (trade name: Pegnol (registered trademark) TH-8, source: TOHO Chemical Industry Co., Ltd.).

Comparative Example 7

A flowable formulation containing 10.3 wt % flometoquin was prepared by using the same starting materials and procedure in Example 1 except that the Morwet (registered trademark) D-425 Powder used in Example 1 was excluded from the formulation and the amount of water was changed to 55.4 wt %.

Comparative Example 8

A flowable formulation containing 10.3 wt % flometoquin was prepared by using the same starting materials and procedure in Comparative Example 1 except that the sodium alkyl naphthalene sulfonate formalin condensate used in Example 1 was replaced with lignin sulfonate (trade name: Newkalgen (registered trademark) WG-4, source: Takemoto Oil & Fat Co., Ltd.).

Comparative Example 9

A flowable formulation containing 10.3 wt % flometoquin was prepared by using the same starting materials and procedure in Comparative Example 1 except that the 3 wt % sodium alkyl naphthalene sulfonate formalin condensate used in Example 2 was replaced with 1 wt % metal salt of polycarboxylic acid (trade name: Newkalgen (registered trademark) WG-5, source: Takemoto Oil & Fat Co., Ltd.) and the amount of water was changed to 54.4 wt %.

Comparative Example 10

A flowable formulation containing 10.3 wt % flometoquin was prepared by using the same starting materials and procedure in Comparative Example 1 except that the sodium alkyl naphthalene sulfonate formalin condensate used in Example 2 was replaced with acrylic acid/maleic acid copolymer (trade name: FOA-10703, source: NIPPON NYUKAZAI CO., LTD.).

Comparative Example 11

A flowable formulation containing 10.3 wt % flometoquin was prepared by using the same starting materials and procedure in Comparative Example 1 except that the sodium alkyl naphthalene sulfonate formalin condensate used in Example 2 was replaced with rosin ester (trade name: Solpol (registered trademark) 7518, source: TOHO Chemical Industry Co., Ltd.).

Comparative Example 12

A flowable formulation containing 10.3 wt % flometoquin was prepared by using the same starting materials and procedure in Comparative Example 1 except that the sodium alkyl naphthalene sulfonate formalin condensate used in Example 1 was replaced with polyvinyl alcohol (partial saponification type, the viscosity of a 4% aqueous solution at 20° C. is 4.8 to 5.8 mPa·s, trade name: Gohsenol (registered trademark) GL-05S, source: The Nippon Synthetic Chemical Industry Co., Ltd.).

Comparative Example 13

A flowable formulation containing 10.3 wt % flometoquin was prepared by using the same starting materials and procedure in Comparative Example 1 except that the 3.0 wt % polyoxyethylene (14) styryl phenyl ether sulfate used in Comparative Example 1 was replaced with 2.0 wt % alkyl naphthalene sulfonate (trade name: Newkalgen (registered trademark) BX-C, source: Takemoto Oil & Fat Co., Ltd.) and the amount of water used was changed to 53.4 wt %.

Comparative Example 14

A flowable formulation containing 10.3 wt % flometoquin was prepared by using the same starting materials and procedure in Comparative Example 1 except that the 3.0 wt % polyoxyethylene (14) styryl phenyl ether sulfate used in Comparative Example 1 was replaced with 2.0 wt % dialkyl sulfosuccinate (trade name: Neocoal (registered trademark) SW-CP, source: Dai-ichi Kogyo Seiyaku Co., Ltd.) and the amount of water was changed to 53.4 wt %.

Comparative Example 15

A flowable formulation containing 10.3 wt % flometoquin was prepared by using the same starting materials and procedure in Comparative Example 1 except that the sodium alkyl naphthalene sulfonate formalin condensate (trade name: Morwet (registered trademark) D-425 Powder, source: Lion Akzo Co., Ltd.) used in Example 1 was replaced with a salt of β-naphthalene sulfonate formalin condensate (trade name: Demol (registered trademark) N, source: Kao Corporation).

Comparative Example 16

1.5 wt % ammonium polyoxyethylene (16) tristyryl phenyl ether sulfate (trade name: Soprophor (registered trademark) 4D384, source: Rhodia Nicca, Ltd.), 3.0 wt % polyoxy-ethylene-polyoxypropylene block polymer (trade name: Pluronic (registered trademark) P105, source: BASF Japan Ltd.), 3.0 wt % propylene glycol (trade name: industrial propylene glycol, source: Adeka Corporation), 0.1 wt % Antifoam (registered trademark) E-20 (silicone-based antifoaming agent, source: Kao Corporation), and 61.55 wt % water were added to a beaker, and the mixture was mixed using a magnetic stirrer. To the mixture was added 10.75 wt % 2-ethyl-3,7-dimethyl-4-methoxy-carbonyloxy-6-(4-trifluoroparamethoxyphenoxy)quinoline (common name: flometoquin, purity 95.8%), the resultant mixture was mixed and stirred using a mixer (Tornado PM-201, manufactured by AS ONE Corporation), glass beads having a diameter of 0.5 to 0.7 mm (glass beads BZ-06, manufactured by AS ONE Corporation) were added thereto, and then the mixture was wet milled until the average particle size thereof became approximately 1.2 μm.

To the milled solution were added 0.1 wt % Antifoam (registered trademark) E-20 (silicone-based antifoaming agent, source: Kao Corporation) and 20 wt % aqueous 1% xanthan gum solution prepared in advance (trade name: Rhodopol (registered trademark) 23, source: Rhodia Nicca, Ltd.), and then the mixture was mixed using a magnetic stirrer to give a flowable formulation containing 10.3 wt % flometoquin.

Comparative Example 17

3.75 wt % (active component 3%) ammonium polyoxyethylene (19) tristyryl phenyl ether sulfate (trade name: SolpolT-20SPG, source: TOHO Chemical Industry Co., Ltd.), 0.71 wt % (active component 0.5%) sodium dioctyl sulfosuccinate (trade name: New-cargen (registered trademark) EP-70G, source: Takemoto Oil & Fat Co., Ltd.), 0.3 wt % crystalline cellulose (trade name: KC flock (registered trademark) W-100G, source: NIPPON PAPER Chemicals CO., LTD.), 5.0 wt % urea (source: NISSAN CHEMICAL INDUSTRY LTD.), 0.1 wt % Antifoam (registered trademark) E-20 (silicone-based antifoaming agent, source: Kao Corporation), and 59.29 wt % water were added to a beaker, and the mixture was mixed using a magnetic stirrer. To the mixture was added 10.75 wt % 2-ethyl-3,7-dimethyl-4-methoxycarbonyloxy-6-(4-trifluoroparamethoxyphenoxy)quinoline (common name: flometoquin, purity 95.8%), the resultant mixture was mixed and stirred using a mixer (Tornado PM-201, manufactured by AS ONE Corporation), glass beads having a diameter of 0.5 to 0.7 mm (glass beads BZ-06, manufactured by AS ONE Corporation) were added thereto, and then the mixture was wet milled until the average particle size thereof became approximately 1.2 μm.

To the milled solution were added 0.1 wt % Antifoam (registered trademark) E-20 (silicone-based antifoaming agent, source: Kao Corporation) and 20 wt % aqueous 1% xanthan gum solution prepared in advance and then the mixture was mixed using a magnetic stirrer to give a flowable formulation containing 10.3 wt % flometoquin.

Comparative Example 18

1.5 wt % naphthalenesulfonate condensate (trade name: Lennox (registered trademark) 1000C, source: TOHO Chemical Industry Co., Ltd.), 0.5 wt % sodium ligninsulfonate (trade name: Vanillex (registered trademark) N, source: Nippon Paper Chemicals Co., Ltd.), 2.0 wt % polyoxyethylene-polyoxy-propylene block polymer (trade name: Epan (registered trademark) U-103, source: Dai-ichi Kogyo Seiyaku Co., Ltd.), 12.0 wt % propylene glycol (trade name: industrial propylene glycol, source: Adeka Corporation), 0.1 wt % Antifoam (registered trademark) E-20 (silicone-based antifoaming agent, source: Kao Corporation), 3.0 wt % rosin glycerin ester (trade name: Sorpol (registered trademark) 7518, source: TOHO Chemical Industry Co., Ltd.), and 50.05 wt % water were added to a beaker, and the mixture was mixed using a magnetic stirrer. To the mixture was added 10.75 wt % 2-ethyl-3,7-dimethyl-4-methoxycarbonyloxy-6-(4-trifluoropara-methoxyphenoxy)quinoline (common name: flometoquin, purity 95.8%), the resultant mixture was mixed and stirred using mixer (Tornado PM-201, manufactured by AS ONE Corporation), glass beads of 0.5 to 0.7 mm (glass beads BZ-06, manufactured by AS ONE Corporation) were added thereto, and then the mixture was wet milled until the average particle size thereof became approximately 1.2 μm.

To the milled solution were added 0.1 wt % Antifoam (registered trademark) E-20 (silicone-based antifoaming agent, source: Kao Corporation) and 20 wt % aqueous 1% xanthan gum solution prepared in advance, and then the mixture was mixed using magnetic stirrer to give a flowable formulation containing 10.3 wt % flometoquin.

Comparative Example 19

5.0 wt % formaldehyde high-polycondensate of sodium naphthalene sulfonate (trade name: Newkalgen (registered trademark) FS-4, source: Takemoto Oil & Fat Co., Ltd.), 5.0 wt % sodium ligninsulfonate (trade name: Newkalgen (registered trademark) WG-4, source: Takemoto Oil & Fat Co., Ltd.), 5.0 wt % propylene glycol (trade name: industrial propylene glycol, source: Adeka Corporation), 0.1 wt % Antifoam (registered trademark) E-20 (silicone-based antifoaming agent, source: Kao Corporation), and 54.05 wt % water were added to a beaker, and the mixture was mixed using a magnetic stirrer. To the mixture was added 10.75 wt % 2-ethyl-3,7-dimethyl-4-methoxy-carbonyloxy-6-(4-trifluoroparamethoxyphenoxy)quinoline (common name: flometoquin, purity 95.8%), the resultant mixture was mixed and stirred using a mixer (Tornado PM-201, manufactured by AS ONE Corporation), glass beads having a diameter of 0.5 to 0.7 mm (glass beads BZ-06, manufactured by AS ONE Corporation) were added thereto, and then the mixture was wet milled until the average particle size thereof became approximately 1.2 μm.

To the milled solution were added 0.1 wt % Antifoam (registered trademark) E-20 (silicone-based antifoaming agent, source: Kao Corporation) and 20 wt % aqueous 1% xanthan gum solution prepared in advance (trade name: Rhodopol (registered trademark) 23, source: Rhodia Nicca, Ltd.), and then the mixture was mixed using a magnetic stirrer to give a flowable formulation containing 10.3 wt % flometoquin.

Test Example 1

Evaluation Test on the Suppression of Crystal Growth at High Temperature Range

Each flowable formulation prepared in Examples 1 to 6, 11, 13 and 14, and Comparative Examples 1 to 6 and 8 to 19 was sealed in a lidded glass bottle (10 mL), and the bottle was stored in a thermostat for 7 days at 40° C. or 54° C. After the storage, the volume median diameter of the particle of the agricultural chemical active ingredient (flometoquin) contained in the formulation was measured using a laser diffraction particle size analyzer (manufactured by Shimadzu Corporation, SALD-2200), and the crystal growth rate of each of the flowable formulations was calculated. The crystal growth rate was obtained by dividing the volume median diameter of the particle stored for 7 days by the volume median diameter of the particle before the test, and then expressing it in percentage. The test results thereof are shown in the following Table 1.

In the formulations of the Comparative Examples, crystal growth was observed at both 40° C. and 54° C., and a particularly high crystal-growth-rate was observed at 54° C.

(i.e. at high temperature). In addition, the formulation of Comparative Example 15 became a pasty formulation with a high viscosity and low fluidity, and it was impossible to make measurements on crystal properties.

In contrast, in the aqueous suspended agricultural chemical compositions of the present invention, almost no crystal growth was observed at 40° C. and only slightly even at 54° C. These test results demonstrate that the aqueous suspended agricultural chemical compositions of the present invention have remarkable effects on the suppression of the crystal growth at high temperature range.

TABLE 1

| | Initial particle size (μm) | Particle size at 40° C. (μm) | Crystal growth rate at 40° C. (%) | Particle size at 54° C. (μm) | Crystal growth rate at 54° C. (%) |
|---|---|---|---|---|---|
| Ex. 1 | 1.2 | 1.2 | 100 | 1.2 | 100 |
| Ex. 2 | 1.2 | 1.2 | 100 | 1.3 | 108 |
| Ex. 3 | 1.2 | 1.0 | 83 | 1.2 | 100 |
| Ex. 4 | 1.2 | 1.1 | 92 | 1.2 | 100 |
| Ex. 5 | 1.0 | 1.0 | 100 | 1.1 | 110 |
| Ex. 6 | 1.1 | 1.0 | 91 | 1.1 | 100 |
| Ex. 11 | 1.0 | 1.0 | 100 | 1.1 | 110 |
| Ex. 13 | 1.2 | 1.2 | 100 | 1.4 | 117 |
| Ex. 14 | 1.2 | 1.2 | 100 | 1.3 | 108 |
| Comp. Ex. 1 | 1.1 | 1.3 | 118 | 1.6 | 145 |
| Comp. Ex. 2 | 1.1 | 1.3 | 118 | 1.7 | 155 |
| Comp. Ex. 3 | 1.1 | 1.6 | 145 | 2.2 | 200 |
| Comp. Ex. 4 | 1.2 | 1.5 | 125 | 2.3 | 192 |
| Comp. Ex. 5 | 1.1 | 1.4 | 127 | 2.2 | 200 |
| Comp. Ex. 6 | 1.2 | 1.3 | 108 | 1.8 | 150 |
| Comp. Ex. 8 | 1.2 | 1.7 | 142 | 1.9 | 158 |
| Comp. Ex. 9 | 1.2 | 1.5 | 125 | 2.0 | 167 |
| Comp. Ex. 10 | 1.2 | 1.7 | 142 | 2.2 | 183 |
| Comp. Ex. 11 | 1.2 | 3.3 | 275 | 4.3 | 358 |
| Comp. Ex. 12 | 1.2 | 1.7 | 142 | 2.1 | 175 |
| Comp. Ex. 13 | 1.1 | 1.3 | 118 | 1.8 | 164 |
| Comp. Ex. 14 | 1.1 | 1.3 | 118 | 1.8 | 164 |
| Comp. Ex. 15 | 1.9 | pasty | — | pasty | — |
| Comp. Ex. 16 | 1.1 | 2.0 | 182 | 2.4 | 218 |
| Comp. Ex. 17 | 1.1 | 1.8 | 164 | 2.4 | 218 |
| Comp. Ex. 18 | 1.1 | 1.5 | 136 | 1.8 | 164 |
| Comp. Ex. 19 | 1.2 | 1.9 | 158 | 2.4 | 200 |

Ex. denotes Example, and Comp. Ex. denotes Comparative Example.

Test Example 2

Evaluation Test on the Suppression of Crystal Growth Over Time

Each flowable formulation prepared in Examples 1 to 14 and Comparative Examples 3 to 19 was sealed in a lidded glass bottle (10 mL), and the bottle was stored in a thermostat for 7 days and 14 days at 54° C. After the storage, the volume median diameter of the particle of the agricultural chemical active ingredient (flometoquin) contained in the formulation was measured by a laser diffraction particle size analyzer (manufactured by Shimadzu Corporation, SALD-2200), and the crystal growth rate of each of the flowable formulations was calculated. The crystal growth rate was obtained by dividing the volume median diameter of the particle stored for 7 days or 14 days by the volume median diameter of the particle before the test, and then expressing it in percentage. The test results thereof are shown in the following Table 2.

In the formulations of the Comparative Examples, crystal growth was observed both after 7 days and after 14 days; whereas in the aqueous suspended agricultural chemical composition of the present invention, crystal growth was not at all observed after 7 days and even after 14 days (i.e. the aqueous suspended agricultural chemical compositions of the present invention have remarkable effects on the suppression of the crystal growth). It can be concluded that the aqueous suspended agricultural chemical composition of the present invention can suppress the crystal growth over a long period of time because crystal growth was observed neither after 7 days nor after 14 days even under the severe condition of 54° C.

Furthermore, when various anionic and/or nonionic surfactants generally used in the art (as illustrated in Comparative Examples 3 to 19), are added to the flowable formulations, crystal growth was observed at a high crystal growth rate, and it was shown that such formulations did not suppress the crystal growth.

The compounds used in the present invention, such as an alkyl sulfate or a polyoxyalkylene alkyl ether sulfate have a function as a wetting agent, and the alkyl naphthalene sulfonate formalin condensate has a function as a dispersant. Thus, it has been confirmed that the presence of both of the above-mentioned two ingredients in the formulation makes it possible to prepare a physicochemically stable flowable formulation capable of suppressing the crystal growth.

Therefore, an aqueous suspended agricultural chemical composition which sufficiently suppresses crystal growth and has an excellent effect on pest control and an excellent stability over time can be obtained by combining a compound represented by Formula (I) or an agriculturally and horticulturally acceptable acid addition salt thereof with one or two or more compounds selected from the group consisting of an alkyl sulfate, a polyoxyalkylene alkyl ether sulfate, an alkyl phosphoric acid and a salt thereof, a polyoxyalkylene alkyl ether phosphoric acid and a salt thereof, and a polyoxyalkylene alkyl ether acetic acid and a salt thereof; and an alkyl naphthalene sulfonate formalin condensate.

TABLE 2

| | Initial particle size (μm) | Particle size after 7 days (μm) | Crystal growth rate after 7 days (%) | Particle size after 14 days (μm) | Crystal growth rate after 14 days (%) |
|---|---|---|---|---|---|
| Ex. 1 | 1.2 | 1.2 | 100 | 1.2 | 100 |
| Ex. 2 | 1.2 | 1.3 | 108 | 1.3 | 108 |
| Ex. 3 | 1.2 | 1.2 | 100 | 1.1 | 92 |
| Ex. 4 | 1.2 | 1.2 | 100 | 1.1 | 92 |
| Ex. 5 | 1.0 | 1.1 | 110 | 1.1 | 110 |
| Ex. 6 | 1.1 | 1.1 | 100 | 1.1 | 100 |
| Ex. 7 | 1.1 | 1.3 | 118 | 1.3 | 118 |
| Ex. 8 | 0.95 | 1.3 | 137 | 1.3 | 137 |
| Ex. 9 | 0.87 | 1.1 | 126 | 1.0 | 115 |
| Ex. 10 | 1.1 | 1.3 | 118 | 1.2 | 109 |
| Ex. 11 | 1.0 | 1.1 | 110 | 1.1 | 110 |
| Ex. 12 | 1.3 | 1.6 | 123 | 1.6 | 123 |
| Ex. 13 | 1.2 | 1.4 | 117 | 1.4 | 117 |
| Ex. 14 | 1.2 | 1.3 | 108 | 1.3 | 108 |
| Comp. Ex. 3 | 1.1 | 2.2 | 200 | 1.7 | 155 |
| Comp. Ex. 4 | 1.2 | 2.3 | 192 | 2.4 | 200 |
| Comp. Ex. 5 | 1.1 | 2.2 | 200 | 2.3 | 209 |
| Comp. Ex. 6 | 1.2 | 1.8 | 150 | 2.1 | 175 |
| Comp. Ex. 7 | 1.2 | 3.0 | 250 | 2.8 | 233 |
| Comp. Ex. 8 | 1.2 | 1.9 | 158 | 3.3 | 275 |
| Comp. Ex. 9 | 1.2 | 2.0 | 167 | 2.5 | 208 |
| Comp. Ex. 10 | 1.2 | 2.2 | 183 | 2.5 | 208 |
| Comp. Ex. 11 | 1.2 | 4.3 | 358 | 4.9 | 408 |
| Comp. Ex. 12 | 1.2 | 2.1 | 175 | 2.3 | 192 |
| Comp. Ex. 13 | 1.1 | 1.8 | 164 | 2.0 | 182 |
| Comp. Ex. 14 | 1.1 | 1.8 | 164 | 2.0 | 182 |
| Comp. Ex. 15 | 1.9 | pasty | — | pasty | — |
| Comp. Ex. 16 | 1.1 | 2.4 | 218 | 2.4 | 218 |

TABLE 2-continued

|  | Initial particle size (μm) | Particle size after 7 days (μm) | Crystal growth rate after 7 days (%) | Particle size after 14 days (μm) | Crystal growth rate after 14 days (%) |
|---|---|---|---|---|---|
| Comp. Ex. 17 | 1.1 | 2.4 | 218 | 2.8 | 255 |
| Comp. Ex. 18 | 1.1 | 1.8 | 164 | 1.8 | 164 |
| Comp. Ex. 19 | 1.2 | 2.4 | 200 | 2.7 | 225 |

Ex. denotes Example, and Comp. Ex. denotes Comparative Example.

The invention claimed is:

1. An aqueous suspended agricultural chemical composition comprising 2-ethyl-3,7-dimethyl-4-methoxy-carbonyloxy-6-(4-trifluoroparamethoxyphenoxy)quinoline or an agriculturally and horticulturally acceptable acid addition salt thereof as an active ingredient, an alkyl naphthalene sulfonate formalin condensate, and at least one compound selected from the group consisting of an alkyl sulfate, a polyoxyalkylene alkyl ether sulfate, an alkyl phosphoric acid or a salt thereof, a polyoxyalkylene alkyl ether phosphoric acid or a salt thereof, and a polyoxyalkylene alkyl ether acetic acid or a salt thereof.

2. The aqueous suspended agricultural chemical composition according to claim 1, wherein the polyoxyalkylene alkyl ether sulfate is a polyoxyethylene alkyl ether sulfate.

* * * * *